United States Patent
Pechstein et al.

(10) Patent No.: US 9,164,057 B2
(45) Date of Patent: Oct. 20, 2015

(54) METHOD FOR OPERATING A MEASURING POINT

(75) Inventors: Torsten Pechstein, Radebeul (DE); Katrin Scholz, Bobritzsch (DE); Thilo Trapp, Waldheim (DE); Ronny Grosse-Uhlmann, Leisnig (DE)

(73) Assignee: ENDRESS + HAUSER CONDUCTA GESELLSCHAFT FUR MESS—UND REGELTECHNIK MBH + CO. KG, Gerlingen (DE)

( * ) Notice: Subject to any disclaimer, the term of this patent is extended or adjusted under 35 U.S.C. 154(b) by 763 days.

(21) Appl. No.: 12/461,528

(22) Filed: Aug. 14, 2009

(65) Prior Publication Data

US 2010/0063762 A1    Mar. 11, 2010

Related U.S. Application Data

(60) Provisional application No. 61/136,446, filed on Sep. 5, 2008.

(30) Foreign Application Priority Data

Sep. 5, 2008    (DE) .................. 10 2008 045 841

(51) Int. Cl.
*G01D 18/00*    (2006.01)
*G01N 27/416*    (2006.01)

(52) U.S. Cl.
CPC .................................. *G01N 27/4165* (2013.01)

(58) Field of Classification Search
CPC ................................................ G01N 27/4165
USPC .................. 702/34, 81, 82, 84, 85
See application file for complete search history.

(56) References Cited

U.S. PATENT DOCUMENTS

| | | | |
|---|---|---|---|
| 6,212,924 B1 * | 4/2001 | Meisser | 72/21.4 |
| 6,428,684 B1 * | 8/2002 | Warburton | 205/775 |
| 6,510,397 B1 * | 1/2003 | Choe | 702/116 |
| 6,553,336 B1 * | 4/2003 | Johnson et al. | 702/188 |
| 6,633,782 B1 | 10/2003 | Schleiss | |
| 6,856,930 B2 * | 2/2005 | Ammann | 702/116 |
| 8,005,629 B2 | 8/2011 | Steinmueller | |
| 8,050,778 B2 * | 11/2011 | Manner | 700/17 |
| 8,329,104 B2 * | 12/2012 | Lehmann et al. | 422/68.1 |
| 2003/0014226 A1 * | 1/2003 | Loecher et al. | 703/2 |
| 2005/0203641 A1 | 9/2005 | Manner | |
| 2005/0283990 A1 * | 12/2005 | McMurtry et al. | 33/556 |

(Continued)

FOREIGN PATENT DOCUMENTS

| | | |
|---|---|---|
| CN | 1678885 A | 10/2005 |
| DE | 100 52 836 | 5/2002 |

(Continued)

*Primary Examiner* — Tung S Lau
*Assistant Examiner* — Xiuquin Sun
(74) *Attorney, Agent, or Firm* — Bacon & Thomas, PLLC

(57) ABSTRACT

A method for operating a measuring point for determining at least one measured variable of a medium is disclosed. The measuring point includes a base unit, which is connected releasably with a sensor unit, and which is provided for communication of a signal representing the value of the measured variable to a process monitoring facility. The following steps are included: at least one-time registering and storing in the base unit a value of a diagnostic parameter stored in the sensor unit or produced by the sensor unit; on the basis of this value conforming a prognosis value or prognosis interval stored in the base unit, and storing the conformed prognosis value or prognosis interval in the base unit in place of the previously stored prognosis value or prognosis interval.

25 Claims, 5 Drawing Sheets

(56) References Cited

U.S. PATENT DOCUMENTS

2006/0155511 A1* 7/2006 Steinmueller et al. ........ 702/176
2010/0027432 A1* 2/2010 Gopalan et al. ............... 370/252

FOREIGN PATENT DOCUMENTS

| | | |
|---|---|---|
| DE | 697 06 433 | 5/2002 |
| DE | 101 41 408 | 3/2003 |
| DE | 101 41 408 A1 | 3/2003 |
| DE | 102 09 318 A1 | 9/2003 |
| DE | 10 2004 012 420 | 9/2005 |
| DE | 10 2004 063 468 | 7/2006 |
| DE | 10 2004 063 469 A1 | 7/2006 |
| WO | WO 2004/025223 A2 | 3/2004 |

* cited by examiner

METHOD FOR OPERATING A MEASURING POINT

CROSS-REFERENCE TO RELATED APPLICATION

This application is a nonprovisional application which claims the benefit of U.S. Provisional Application No. 61/136,446 filed on Sep. 5, 2008.

TECHNICAL FIELD

The invention relates to a method for operating a measuring point for determining at least one measured variable of a medium, wherein the measuring point includes a base unit, which is connected releasably with a sensor unit, and which is provided for communication of a signal representing the value of the measured variable to a process monitoring facility.

BACKGROUND DISCUSSION

Measuring points of this type include, for example, pH measuring points or other measuring points of analytical measurements technology. In this category belong, especially, other potentiometric, amperometric, coulometric, colorimetric, photometric, turbidimetric and spectrometric units.

The problem to which the invention is directed will be explained on the basis of an example of pH measuring points. It is not intended, however, that the invention be limited to a method for operating pH measuring points.

A sensor unit includes at least one transducer, which outputs an electrical signal dependent on the value of the measured variable. Frequently, the transmit function of the transducer is variable. This is true in special measure for pH sensors. Therefore, pH sensors, or pH electrodes, must, at suitable points in time, be subjected to maintenance, especially, it must be calibrated anew. The length of time intervals between the maintenance procedures, or calibration intervals, depends strongly on the environmental influences, to which the sensor is exposed during its lifetime. Also, the total lifetime of the sensor is strongly influenced by these environmental conditions.

The term, "calibrating", has frequently a somewhat different meaning in pH measuring than usual. In general, one means with "calibrating" the checking of the display of a measuring device against a standard; the deviation between true value and display value is detected. The conforming of the display value to the true value is referred to as adjusting. "Calibrating" in the case of a pH sensor is strictly an adjusting. Since the term, "calibrating", is widely used in electrochemistry, it is also used here.

In the guidelines VDI/VDE 2650 and NAMUR NE107, recently, future market developments in the area of sensor diagnostics are emphasized.

The state of the art contains attempts to equip sensors with intelligent self-diagnosis. Thus, there are first publications with reference to analysis of individual sensor characteristics for ascertaining the period of time until the entering of a defined sensor state in the future, e.g. the end of the sensor lifetime or a point in time, at which a new calibrating is necessary. Cited by way of example are DE 10141408, JP 05-209858, JP 2002-228495, DE 10 2004 012420 and DE 10239610.

The described methods in the named publications operate on the assumption that the behavior of a sensor in a medium with essentially known ingredients and in the case of known environmental conditions can be sufficiently well described by a model. Actually, however, the relationships are a number of times more complex, so that a mapping via a model of the processes, which influence the transmit function of a sensor, especially, a pH electrode, is not, or, at most, only with large effort, possible.

pH glass electrodes embodied as single-rod, measuring chains are subject to wear, which depends, in large part, on pH value and temperature of the environment. Besides the glass membrane, also the reference half-cell of a glass electrode is strongly loaded. While, at the glass membrane, due to media influences, a gradual deterioration takes place and thereby the probability for a sensor failure increases, diaphragm changes, poisoning and deterioration of the reference electrolyte of the reference half-cell can also degrade the functionality of the sensor.

Due to the large number of parameters, which determine the lifetime, or service life, of a sensor, prediction is difficult, the more so, since also a considerable scatter from sensor instance to sensor instance of the same type occurs.

SUMMARY OF THE INVENTION

It is, consequently, an object of the present invention to provide a method for operating a measuring point, which meets the above-related requirements, and which, especially, permits, with small effort, a reliable statement concerning the period of time until the reaching of a defined sensor state in the future.

This object is achieved by a method for operating a measuring point for determining at least one measured variable of a medium, wherein the measuring point includes a base unit, which is releasably connected with a sensor unit, and which is provided for communication of a signal representing the value of the measured variable to a process monitoring facility, comprising at least steps as follows:

a) At least one-time registering and storing of a value of a diagnostic parameter, stored in the sensor unit or produced by the sensor unit, in a first data storage unit of the base unit;

b) on the basis of the at least one value of the diagnostic parameter stored in the first data storage unit, conforming a prognosis value or prognosis interval stored in a second data storage unit of the base unit, and storing the conformed prognosis value or prognosis interval in the second data storage unit of the base unit in place of the previously stored prognosis value or prognosis interval.

The sensor unit includes at least one primary sensor and a sensor head, wherein the medium acts on the primary sensor, which includes a transducer with a signal output, which outputs an electrical signal dependent on the value of the measured variable, wherein the transducer has a variable transmit function. Integrated in the sensor head can be a circuit for conditioning the transducer signals, including an A/D converter and a second microprocessor for processing the digitized signals. A signal produced in the sensor unit can, consequently, be, for example, the electrical transducer signal dependent on the measured variable, or a conditioned, especially, digitized, transducer signal.

Furthermore, the sensor head can include a data memory, in which sensor-specific values of one or a plurality of diagnostic parameters are stored. Such diagnostic parameters can be, for example, calibration data of the last calibration, such as, for example, in the case of a pH sensor, zero-point and slope, or loading data of the sensor unit, which were ascertained and stored in the manner described in DE 10 2004 012 420 B4 or in like manner.

A value of such a diagnostic parameter is transmitted from the sensor unit to the base unit and stored in a memory unit of the base unit. It is possible to transmit exactly one value. Equally, however, also a sequence of values can be transmitted and stored. In such case, all values of the sequence, or also only, in each case, the most up-to-date value, can be stored. If a time sequence of multiply, sequentially, registered values of a diagnostic parameter is stored, the values of the points in time, at which they were registered, or at least one identifier, on the basis of which the correct time sequence of the values is ascertainable, can be stored. In an additional memory unit of the base unit, a prognosis value or a prognosis interval is stored. For example, the prognosis value can be a total loading reserve of the sensor unit, i.e. a total lifetime of the sensor unit weighted with the sensor loading, or also a remaining time interval until the next calibrating is due. The prognosis value can also be a value of a calibration parameter expected at a certain point in time, for example a zero-point or slope value expected at a certain calibration point in time, for example, at an nth calibration, or a change of zero-point or slope expected between two calibrations following one after the other.

Through the conforming of the prognosis value or prognosis interval on the basis of the newly stored value of the diagnostic parameter and the storing of the so ascertained, conformed prognosis value or prognosis interval in the data memory of the base unit, a more solid prognosis value, or prognosis interval, is made available, which is available to following sensor units after replacement of the current sensor unit. The measuring point can thus, over the lifetime of a plurality of sensor units, and beyond, conform its diagnostic functions always better to the concrete environmental demands and simultaneously statistically take into consideration fluctuations between the individual sensor instances.

The described method can include additional steps beyond the steps a) and b). However, at a point in time during operation of the measuring point, at least once, the steps a) and b) are performed.

In an additional step c), the in step a) registered and in the first data storage unit of the base unit stored value of a diagnostic parameter produced by the sensor unit can be compared with the prognosis value or prognosis interval stored in the base unit. This step can be performed, for example, before the prognosis value is conformed on the basis of the ascertained value of the diagnostic parameter.

A comparison of the registered value of the diagnostic parameter with the stored prognosis value, or the prognosis interval, can, for example, for the case, in which the prognosis value concerns an expected calibration parameter value or an expected changing of a calibration parameter value, give an indication of whether the sensor unit still works correctly or is possibly already damaged. If the diagnostic parameter value of the sensor unit concerns, for example, the current sensor loading in the form a weighted loading time, which, for example, can be ascertained by adding loading equivalents over the, to this point, duration of operation of the sensor unit, then a comparison with a stored prognosis value, which gives a total loading reserve of the sensor unit, can give an indication of the remaining lifetime of the sensor.

Advantageously, in an additional step, the sensor unit is replaced by a temporally following sensor unit of the same type and, after replacement of the sensor unit by the following sensor unit of the same type, the steps a) and b) or a) to (c) are repeated at least once.

This method provides, such as already mentioned, a learning procedure, wherein, over the lives of a plurality of sensor units, and beyond, an ever more solid value for a prognosis, or a prognosis interval, is obtained. At the same time, a comparison of the, in each case, newly registered values of at least one diagnostic parameter with the stored prognosis value, or prognosis interval, permits, depending on the type of the stored prognosis value, or prognosis interval, a statement to be made concerning the current state of the sensor unit currently connected with the base unit, or to estimate a remaining service life of the sensor unit.

Because of the dependence already mentioned above of the diagnostic parameter characteristic for the sensor unit on the environmental conditions and, therewith, on the measuring point, it is advantageous to integrate the learning procedure in a data processing unit of the base unit.

In an advantageous embodiment of the method, the conforming of the prognosis value or prognosis interval is accomplished by means of a learning algorithm. The learning algorithm includes, in such case, especially, a step of average forming, sliding weighted average forming, exponential smoothing of the first and second kind, linear regression for conforming of a polynomial or other non-linear function, or the like.

In an embodiment of the method, the base unit is provided additional information for ascertaining the prognosis value. This additional information can be, for example, a weighting of the current diagnostic parameter value. This comes in question, for example, when a sensor unit was damaged during a maintenance procedure and therefore the value of the diagnostic parameter produced by it is corrupted and, correspondingly, should not, or only with little weight, be taken into consideration in the learning algorithm. Another example of additional information is, in the case of a defective sensor unit, the input of the actual lifetime of the sensor unit, for example by a service person.

In an embodiment of the method, the first data storage unit comprises a memory unit having a plurality of memory locations, for example a database matrix, wherein the value of the diagnostic parameter is stored together with an identification of the associated sensor unit, for example, the serial number of the associated sensor unit, in a memory location. This is advantageous, when the sensor unit is, at times, removed from the measuring point, for example for performing maintenance procedures, and, in the intervening times, another sensor unit is used at the measuring point. When the first, sensor unit, after termination of the maintenance, is connected back to the measuring point, the original memory location, which can be identified uniquely on the basis of the identification of the sensor unit, can be written further with values of the diagnostic parameter. When a number of values of the diagnostic parameter stored or produced in the sensor unit are registered and stored, for example, in a row of a database matrix, the entire row of the database matrix can be marked with the identification of the sensor unit. If the sensor unit is removed for a time and connected later back to the base unit, on the basis of the identification, the original row with the earlier stored values of the sensor unit can again be found and further written with the new value.

In a special embodiment of the method, a parameter related to sensor loading, for example, a weighted loading time of the sensor unit, is registered as diagnostic parameter, and, as prognosis value or prognosis interval, a parameter is ascertained and stored, which correlates with the total sensor loading, with which the sensor unit can be loaded, before it must be replaced, such as, for example, the total loading reserve or a confidence interval, which surrounds the total loading reserve.

In a further development of this embodiment, in an ongoing manner, current values of the parameter of the sensor unit related to sensor loading are registered and stored in the data storage unit of the base unit. When the sensor unit, because of a defect, must be replaced, this information ("sensor defective") is made available to the base unit as additional information. The value of the parameter related to sensor loading stored, at this point in time, in the data storage unit of the sensor is used as learning value for the measuring point, i.e. this last stored value serves for the conforming of the stored prognosis value or prognosis interval.

During the ongoing registering of the current values of the parameter related to sensor loading of the sensor unit, the currently registered values can be compared with the stored prognosis value or prognosis interval. If the comparison shows that the last registered value has reached or exceeded the prognosis value or that a lower interval boundary of the prognosis interval has been exceeded, a report in the form a warning or an alarm can be generated.

In another special embodiment of the method already indicated above, a parameter of the sensor unit, especially a calibration parameter, is repeatedly registered as diagnostic parameter and the individual repeatedly registered values are stored in individual locations of a data storage unit of the base unit, for example, in a row of a database matrix, together with the points in time of registering or a parameter equivalent thereto, and an identification of the associated sensor unit, for example, the serial number of the sensor unit. In such case, ascertained as prognosis value is, in each case, a value for the parameter of the sensor unit, especially, the calibration parameter, for example, by average forming or extrapolation, and such value is then stored in the data memory of the base unit. The data storage unit can, for this purpose, be adapted as a database matrix, in whose rows values of a calibration parameter temporally following one another can be stored, wherein the columns of the database matrix are associated with a registering point in time of the calibration parameter or a parameter equivalent therewith.

In this case, thus, not only a prognosis value is present, but also a plurality of prognosis parameters. For example, such as further below presented in detail, in the case of each new calibration of the sensor unit, the values of the calibration parameters, zero-point and slope, or the change of zero-point and slope since the preceding calibration, can be ascertained and stored in their own memory location of the data memory of the base unit together with a current index of the new calibration. With this data, individual prognosis values for the calibration parameters or the changes of the calibration parameters for each new calibration—thus for the first, second, third, etc. calibration—of a sensor unit of the same type can be ascertained, stored, conformed by means of newly added values of further sensor units of the same type, and the conformed prognosis values newly stored.

In an additional special embodiment, from repeatedly registered values of the diagnostic parameter, for example, from repeatedly registered values of a parameter of the sensor unit, especially, of a calibration parameter, a total lifetime, or a sensor remaining service life for sensor units of the of the same type can be ascertained as prognosis value, in that the conforming of the prognosis value occurs by ascertaining a trend, especially, a linear function, for the time development of the diagnostic parameter.

A corresponding measuring point for performing the described method includes a base unit, which is connected releasably with a sensor unit, and which is provided for communication of a signal representing the value of the measured variable to a process monitoring facility, wherein the base unit, furthermore, includes:

a microprocessor for conditioning data received from the sensor unit for communication to the process monitoring facility;

a first data storage unit adapted to register and store a value of a diagnostic parameter in the sensor unit, stored or produced by the sensor unit;

a second data storage unit adapted to store a prognosis value or a prognosis interval; and a program memory unit, in which an algorithm, especially, a learning algorithm, is stored, which serves for conforming the prognosis value or prognosis interval stored in the second data storage unit on the basis of the value of the diagnostic parameter last registered in the first data storage unit and for storage of the conformed prognosis value or prognosis interval in the second data storage unit.

In an embodiment, the base unit, furthermore, has available a second program memory unit, in which a comparison algorithm is stored, which serves for comparison of the last value of the diagnostic parameter registered in the first data storage unit with the prognosis value or prognosis interval stored in the second data storage unit.

BRIEF DESCRIPTION OF THE DRAWINGS

The invention will now be explained in greater detail on the basis of the examples of embodiments in the drawing, the figures of which show as follows.

DETAILED DISCUSSION IN CONJUNCTION WITH THE DRAWINGS

Figure 1:
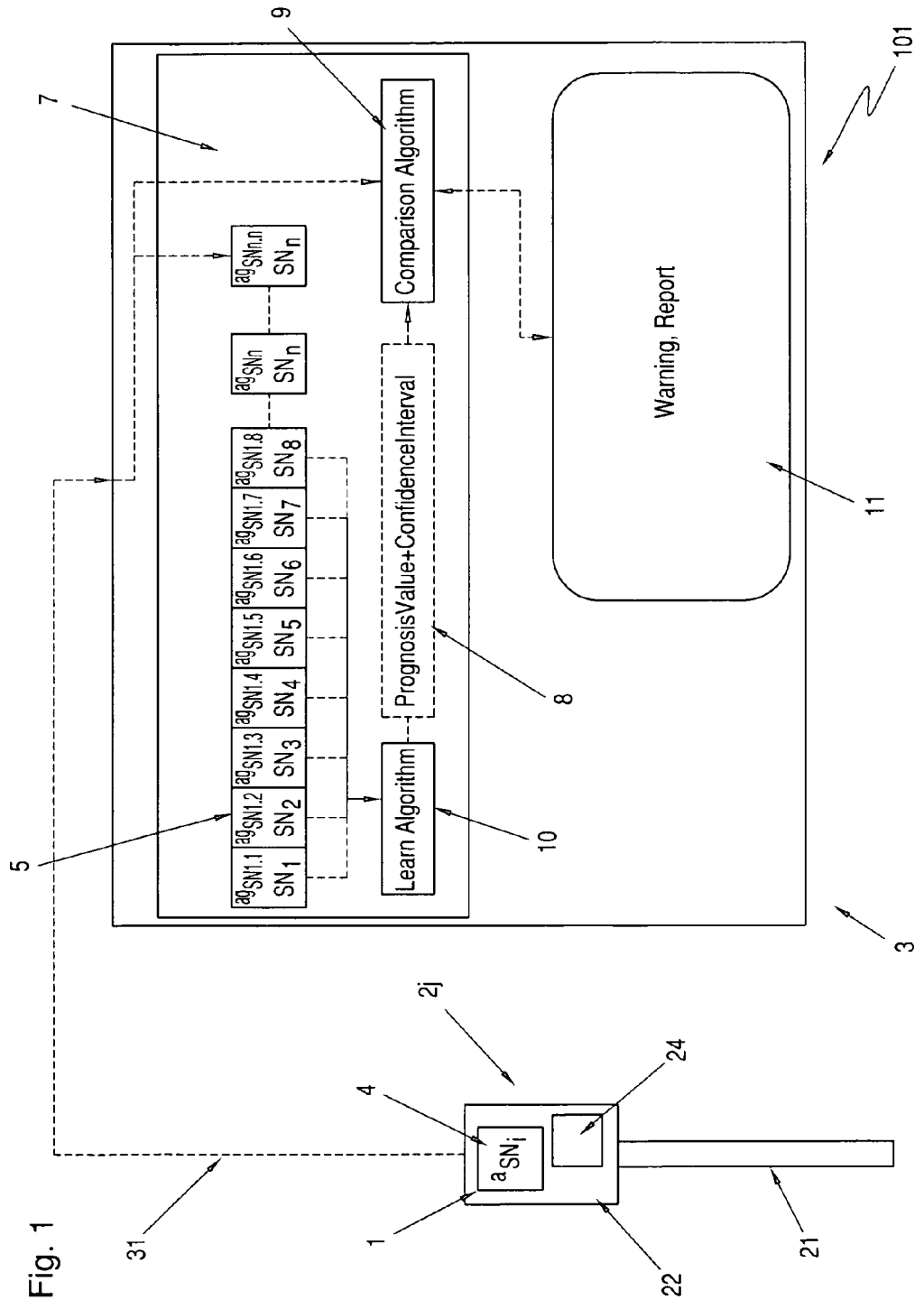
FIG. 1 a schematic drawing of a measuring point according to a first example of an embodiment of the invention.

FIG. 1 shows schematically a measuring point 101, which is embodied to learn, over the lifetime of a plurality of sensor units, a prognosis value for a diagnostic parameter a for a sensor unit. The diagnostic parameter a can be, for example, the total loading reserve, total operating time, operating times under defined conditions, counter states, e.g. for counting of "cleaning in process (CIP)" steps, "sterilization in process (SIP)" steps, autoclaving steps, or the like.

The measuring point 101 includes a sensor unit 2.$j$ and a base unit 3. In the case of the sensor unit 2.$j$, such is, in the example of an embodiment, a pH sensor, which includes a primary sensor 21, in the form a single-rod measuring chain, and a sensor head 22, wherein the sensor head 22 is connected fixedly with the single-rod measuring chain 21. The single-rod measuring chain 21 provides on its signal output a potential difference between a reference potential and a pH value dependent potential correlated with the current value of the medium. The signal output of the single-rod measuring chain 21 is fed to a circuit in the sensor head for conditioning the signals of the single-rod measuring chain 21, wherein the circuit includes an A/D converter and a microprocessor for processing the digitized signals. Output by the single-rod measuring chain 21 can include, furthermore, a temperature signal. The sensor head 22 contains a data memory 4, in which sensor-specific data are stored, for example, calibration data and their history or data for loading history. Furthermore, the sensor head contains a program memory 24, which contains base functionalities for operation of the sensor unit.

Furthermore, the sensor head contains a preferably inductively coupling interface 31, via which occurs energy supply of the sensor unit 2.$j$ from the base unit 3 and data exchange between the sensor unit 2.$j$ and the base unit 3.

The base unit 3 includes a microprocessor for conditioning data, which are received from the sensor unit, in order then to transmit such, in given cases, via a fieldbus to a central computer of the process monitoring facility (not shown in FIG. 1). The base unit 3 includes, furthermore, a data memory 7, in which a diagnosis relevant parameter, so-called diagnostic parameter $a_{SNj}$, produced in the sensor unit 2.$j$, more exactly in the sensor plug-in head 22, or stored in the data memory 4 of the sensor plug-in head 22, can be stored. The diagnostic parameter $a_{SNj}$ is transmitted via the interface 31 of the sensor unit 2.$j$ to the base unit 3 and stored in the data memory 7 of the base unit 3. In the example of FIG. 1, the data memory 7 includes a one-row database matrix 5, in which the diagnostic parameter $a_{SNj}$ can be stored together with additional information, such as, for example, the serial number of the sensor unit 2.$j$, from which a diagnostic parameter $a_{SNj}$ was transmitted. The diagnostic parameter $a_{SNj}$ is stored over the lifetime of a plurality of sensor units, and beyond.

The base unit includes, furthermore, a program memory, which includes a software module, which contains a learning algorithm. This learning algorithm includes a functionality, with which, from some or all of the values stored in the database matrix 5, a prognosis value can be ascertained and stored in the data memory 8 of the base unit 3. Furthermore, the learning algorithm can also include a function, with which a limit value window around the ascertained prognosis value can be formed. This limit value window can likewise be stored in the data memory 8 as prognosis interval.

Furthermore, the program memory 9 of the base unit 3 includes a software module, which contains a comparison algorithm. This comparison algorithm is embodied to compare newly registered values of the diagnostic parameter $a_{SNj}$, which is captured, for example, from the data memory of a sensor unit newly connected to the base unit 3, with the prognosis value or with the prognosis interval formed by the limit value window around the prognosis value. If the comparison algorithm detects a deviation of the newly ascertained diagnostic parameter $a_{SNj}$ from the prognosis value or prognosis interval stored in the data memory 8, it can cause the output of a report via the display 11, for example, a warning.

A method for operating the measuring point 101 illustrated in FIG. 1 will now be described in greater detail.

The first n sensor units 2.1, . . . , 2.$n$ connected to the base unit 3 can be used as "training units". Since the prognosis value ascertained by the learning algorithm in this early phase of the measuring point 101 still is based on too little fundamental data, this value is only tentatively usable and should, consequently, only be used with reservations for sensor diagnostics or for remaining lifetime prediction. Beginning with the n+1st sensor unit 2.$n$+1 of the same sensor type, via comparison algorithms, or learning algorithms, more reliable diagnostic statements, or new, conformed prognosis values are obtained.

Following connecting of a sensor unit 2.$j$ via the interface 31 to the base unit 3, the learning algorithm checks first, whether the sensor unit 2.$j$ should be used for ascertaining, or for conforming, the prognosis value or prognosis interval. For example, it can be ascertained, how many operating hours the newly connected sensor unit 2.$j$ has already experienced. On the basis of the operating hours count stored in the memory unit 4 of the sensor unit 2.$j$, it can be decided, whether the sensor unit is taken into consideration for the conforming of the prognosis value or prognosis interval.

Furthermore, it is first checked, whether the serial number SNj of the sensor unit 2.$j$ is already stored in the database matrix 5 of the base unit 3. If entries are already present in the database matrix 5, which by the serial number supplementally stored there can be unequivocally associated with the sensor unit 2.$j$, then these entries are brought forward. If there are in the database still no entries for the new sensor unit 2.$j$ present, then a new database entry—a new column of the one-row database matrix 5—is begun.

An algorithm in the program memory 24 of the sensor unit 2.$j$ delivers to the base unit via the interface 31 periodically a value $a_{SNj}$ of the diagnostic parameter. This value is stored in the column belonging to the serial number SNj of the sensor unit 2.$j$. If the sensor unit 2.$j$ is replaced with a following sensor unit 2.$k$, then the most up-to-date value $a_{SNj}$ is first stored in the database matrix 5. Upon connection of the following sensor unit 2.$k$, a query is made, whether the preceding sensor unit 2.$j$ is defective, or whether it has only temporarily been removed, for example, for performing calibration, or maintenance, procedures. If the preceding sensor unit 2.$j$ was removed because of a defect, the last stored value $a_{SNj}$ is defined as learning value $ag_{SNj}$. Otherwise, the state of the database entry is kept and can be brought forward, when the sensor unit 2.$j$ is connected back to the base unit 3. If the sensor unit is taken out of the process before the end of its lifetime, be it based on a changing of the installed sensor type or based on a process independent defect turned up during maintenance or calibrating, there is the possibility of erasing the relevant database entry.

It is possible, never to leave the learning state, i.e. to conduct a conforming of the prognosis value, or the prognosis interval, during the entire period of operation of the measuring point. Alternatively, after reaching an established maximum number max of learning values of $ag_{SNj}$, the learning state can be terminated. In this case, only the learning values from $ag_{SN1}$ to $ag_{SNmax}$ are taken into consideration for ascertaining the prognosis value or prognosis interval. The prognosis value, or the prognosis interval, as the case may be, remains constant after termination of the learning state.

There are different options for ascertaining the prognosis value. Simple and robust variants are the sliding weighted average value, and exponential smoothing of 1st and 2nd type, depending on whether a trend is detectable or not. Also, complex algorithms, such as linear regression, the matching of polynomials or other non-linear functions or the like can be applied.

Already during the learning state, or after termination of the learning state, the diagnostic parameter $a_{SNj}$ of a currently connected sensor unit 2.$j$ can be compared, by means of the comparison algorithm 9, with the prognosis value, or the prognosis interval (which can be a confidence interval surrounding the prognosis value). As a function of the position of the diagnostic parameter $a_{SNj}$ with reference to the range of the prognosis interval, a warning or alarm message is generated on the display 11 of the base unit 3. A warning could be generated, for example, upon exceeding the lower limit of the prognosis interval. An option would be, accordingly, an alarm, for example, in the case of a value between the lower prognosis limit and the prognosis value.

Figure 2:
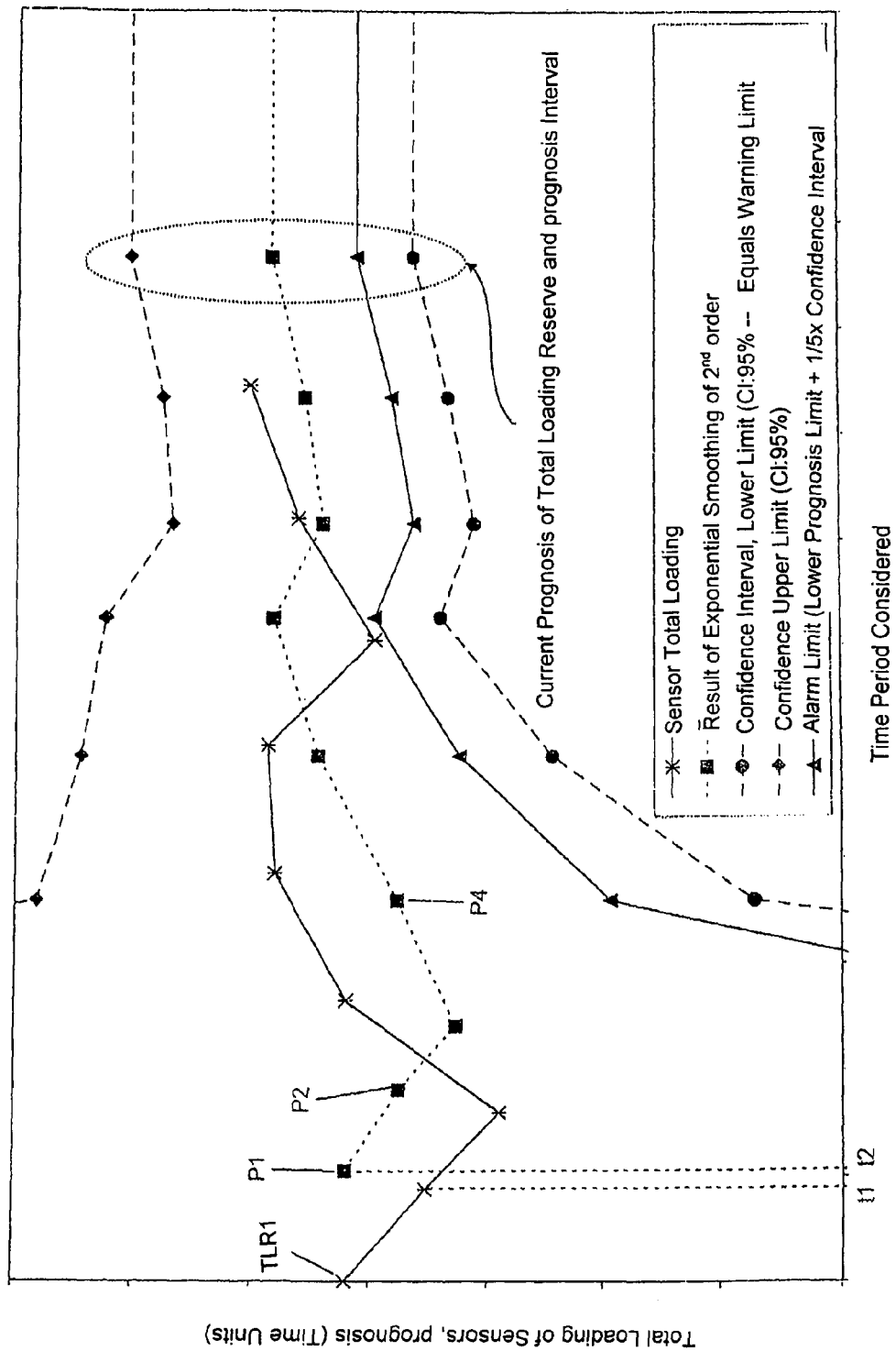
FIG. 2 a diagram illustrating ascertaining of a prognosis value from stored values of a diagnostic parameter for different sensor units, using the example of total loading reserve.

This is illustrated in FIG. 2. FIG. 2 shows, as a function of time, the curve of learning values of $ag_{SNj}$ obtained on the basis of various sensor units $2.j$ using the example of the diagnosis parameter ($a_{SNj}$), sensor loading, i.e. a weighted duration of operation of the sensor unit, taking into consideration loading-relevant parameters, such as pH value and temperature, for example, in the form of loading equivalents such as described in DE 10 2004 012 420. The associated prognosis value is the total loading reserve of the sensor unit, i.e. the total lifetime of the sensor unit taking into consideration the loading-relevant parameters. The learning values ($ag_{SNj}$) $TLR_j$ of the total loading reserve are shown in the form of stars. For purposes of simplification, it is assumed, that each sensor unit $2.j$ remains connected with the base unit 3 up to the end of its lifetime and only once a sensor unit becomes defective is it replaced by a following sensor unit $2.j+1$.

For point in time t=0, a first learning value $TLR_1$ of the total loading reserve is present, which was ascertained on the basis of a first sensor unit 2.1, which, after a lifetime, which corresponds to the total loading reserve $TLR_1$, was replaced with a second sensor unit 2.2, because of a defect. From this value, the learning algorithm 10 ascertains a first prognosis value P1 (square) for the total loading reserve of a sensor unit of the type of sensor unit 2.1. The prognosis value P1 is identical with the learning value $TLR_1$ (since, for the point in time t=0, no additional information is present) and amounts to about 2100 time units.

At the point in time t=0, the defective first sensor unit 2.1 is replaced with a following, new sensor unit 2.2. During the operating of the new sensor unit 2.2, periodically, a loading value of the sensor unit 2.2 is transmitted to the database matrix 5 of the base unit 3. This loading value can be compared by means of the comparison algorithm with the prognosis value P1. Upon reaching the prognosis value, the comparison algorithm issues a warning or alarm. However, this diagnostic result is still tentative and uncertain, since the prognosis value P1 relies on a single learning value.

At point in time t1, which lies still before the prognosticated end of life t2 of the sensor unit, the sensor unit 2.2 must be replaced with a following, third sensor unit 2.3, because of a defect. The loading value registered, at this point in time, in database matrix is stored as new learning value $TLR_2$ in the column associated with sensor unit 2.2. With application of the new learning value $TLR_2$, the prognosis value P1 is conformed and a new, lower prognosis value P2 ascertained. This new, conformed, prognosis value P2 replaces the original prognosis value P1 in the data memory 8 of the base unit.

In analogous manner, the method is continued for following sensor units $2.j$. For the prognosis value P4, as well as the following additional prognosis values, there is in FIG. 2 a confidence interval, which surrounds the prognosis values. The lower limit of this confidence, or prognosis, interval is with filled dots, the upper limit with filled diamonds. Furthermore, there is in FIG. 2 also a lower alarm limit, which is marked with triangles.

As soon as the comparison algorithm determines that the, such as described in connection with FIG. 1, periodically registered diagnostic parameter (here the sensor loading) of the sensor unit has reached the lower limit of the prognosis interval, the output of a warning is brought about via the display 11. If the sensor loading reaches the alarm limit, then an alarm is correspondingly output.

Furthermore, as input variables for a learning algorithm such as it is here described, sensor data such as the total loading reserve, operating times under defined conditions, counter states, e.g. for counting of "cleaning in process (CIP)" steps, "sterilization in process (SIP)" steps, autoclaving steps, or like sensor data can also be used.

Figure 3:
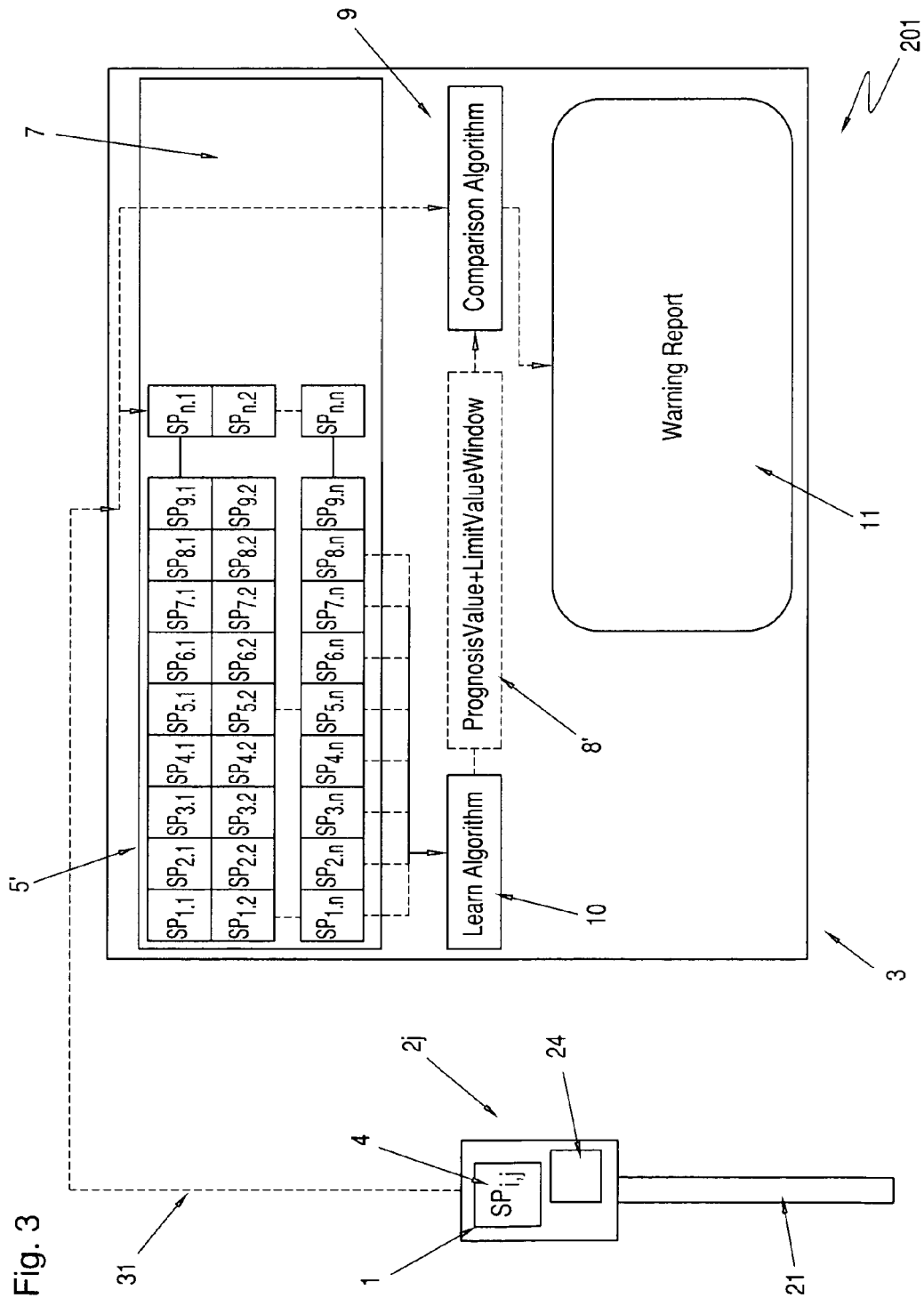
FIG. 3 a schematic drawing of a measuring point according to a second example of an embodiment of the invention.

FIG. 3 shows a further example of the invention. The schematically illustrated measuring point 201 is, in large part, identical to the measuring point 101 shown in FIG. 1. The data memory 7 contains, however, not just a one-row database matrix 5, but, instead, a multirow and multicolumn database matrix 5'. In this embodiment, the measuring point 201 can store and analyze parameter changes occurring over the lifetime of the sensor. For example, shifting of the sensor zero point, and the changing of the sensor slope, between beginning and end of the total operating time of the sensor unit can be registered. Via a prognosis, a statement concerning future maximum changes is possible, against which as limit value, currently registered change values can be tested. The variant of the learning algorithm 10 presented in the following can be applied simultaneously to a number of variables. In this way, following analyses are possible, which are based on the interrelationship of the ascertained, i.e. "learned", upper limits.

If, for example, for the case, in which the sensor unit is a pH electrode, the changing of the zero-point of the pH sensor is taken as diagnostic parameter $SP_{i,j}$, then there can be stored in the individual memory locations of the database matrix 5, for a number of sensor units, the values of the shifting of the sensor zero point registered in different calibrations, together with the serial number of the sensor and the point in time of the calibrating or the number of the already undertaken calibrations.

These diagnostic parameters $SP_{i,j}$, here thus the shiftings of the sensor zero point, are stored over the lifetime of a plurality of sensor units, and beyond. In the example of FIG. 3, the index j stands for the particular sensor unit, wherein sensor units following one another are referenced, in each case, with a consecutive natural number j. The index i is used in the present example for a consecutive numbering of repeatedly registered and stored values of the shifting of the sensor zero point.

The learning algorithm 10 ascertains thus, from values ascertained for a number of sensor units for the shifting of the sensor zero point at a certain point in time unified for all sensor units or after a same number of calibrations for all sensor units (if this number were, for example, 3, this would correspond to the values SP3, j, wherein j stands for the sequential number of the sensor unit), a prognosis value, thus an expected shifting of the sensor zero point for sensor units of the same type. In contrast to the examples described in connection with FIGS. 1 and 2, in the case of which, first after final replacement of the sensor unit $2.j$ after a defect, a learning value is stored for the learning algorithm in the database matrix 5, here, each value for the sensor shifting ascertained in a calibrating is stored as learning value in the database matrix 5'.

In the case of the considered example of the shifting of the sensor zero point as diagnostic parameter, a deviation of the prognosis value or prognosis interval would mean, that the zero point shift lies outside the limit value window around the expected value of the zero point shift. In this case, the report generated by the comparison algorithm would be, thus, a warning, since the sensor deviates from the prognosticated behavior.

In the following, the method for operating the measuring point 201 will be described in more detail.

In the memory unit 4 of the sensor unit 2.j, the calibration data of the sensor unit, thus also the shifting of the zero-point, are stored, especially, for the point in time of the last calibration. The most up-to-date value of the changing of the zero-point and information concerning the calibration point in time are read out by the base unit 3 from the data memory 4. The information concerning the calibration point in time can be a time specification referenced to the total operating time of the sensor to this point, which gives, thus, after how many operating hours the corresponding calibrating took place. It can also be a consecutive numbering of the calibrations of the sensor unit accomplished to this point. The value of the shifting of the zero-point read out of the data memory 4 is stored together with the serial number and the information concerning the calibration point in time in the database matrix 5. The new value is stored in the database matrix 5 in the same row as all other values read-out for the changing of the zero-point of such sensor unit at other calibration points in time and in the same column as the values read-out for shifting of the changing of the zero-point of other sensor units of the same type at the same or comparable calibration point in time.

Accessing the values stored in the database matrix 5 are both the learning algorithm stored in the program memory 10 as well as also the comparison algorithm stored in the program memory 9. The comparison algorithm serves in such case for composing diagnostic statements for the currently connected sensor unit. In a data memory 8' of the base unit 3, a corresponding prognosis value for the changing of the zero-point is already stored, which was ascertained from the corresponding data of sensor units 2.j earlier applied at the measuring point 201. Advantageously stored supplementally, besides the prognosis value, in the data memory 8' can be a limit value window surrounding the prognosis value. With the comparison algorithm, it is ascertained, whether the value of the shifting of the zero-point stored newly in the database matrix 5' for the last calibration point in time of the sensor lies within the limit value window. If this is not the case, a warning report can be generated.

The learning algorithm 10 serves for further conforming the prognosis value stored in the data memory 8' and for optimizing the solidity of the value, so that it is no longer tentative. For this, the learning algorithm ascertains a conformed prognosis value from the newly stored value $SP_{ij}$ of the changing of the zero-point at a certain calibration point in time and from the corresponding values, which are already present in the database matrix 5' and which were ascertained for preceding sensor units of the same type during the same or comparable calibration point in time. Simple, robust methods for determining the conformed prognosis value are, for example, the forming of an average value or a weighted average value or exponential smoothing of 1st and 2nd types, depending on whether a trend is detectable or not.

The advantage of this procedure, relative to the conventional practice of measuring point independently specifying for sensors of the same type a fixed tolerance interval for the changing of the zero-point between two calibrations, is that now, with assistance of the learning algorithm, a measuring location specific value for the zero point shift, or a measuring point specific, tolerance interval, can be predetermined. This permits significantly more exact diagnostic statements. Thus, in the case of one type of process, a strong changing of the zero-point between two calibrations can be quite tolerable, while, in the case of another type of process, as a rule, only a low changing of the zero-point should occur. With the help of the prognosis values "learned" from the measuring point, an option is to differentiate between two process types, whereas, in the case of input of a fixed tolerance interval for the zero point shifting independently of the process conditions, such a distinguishing is not possible.

Figure 4:
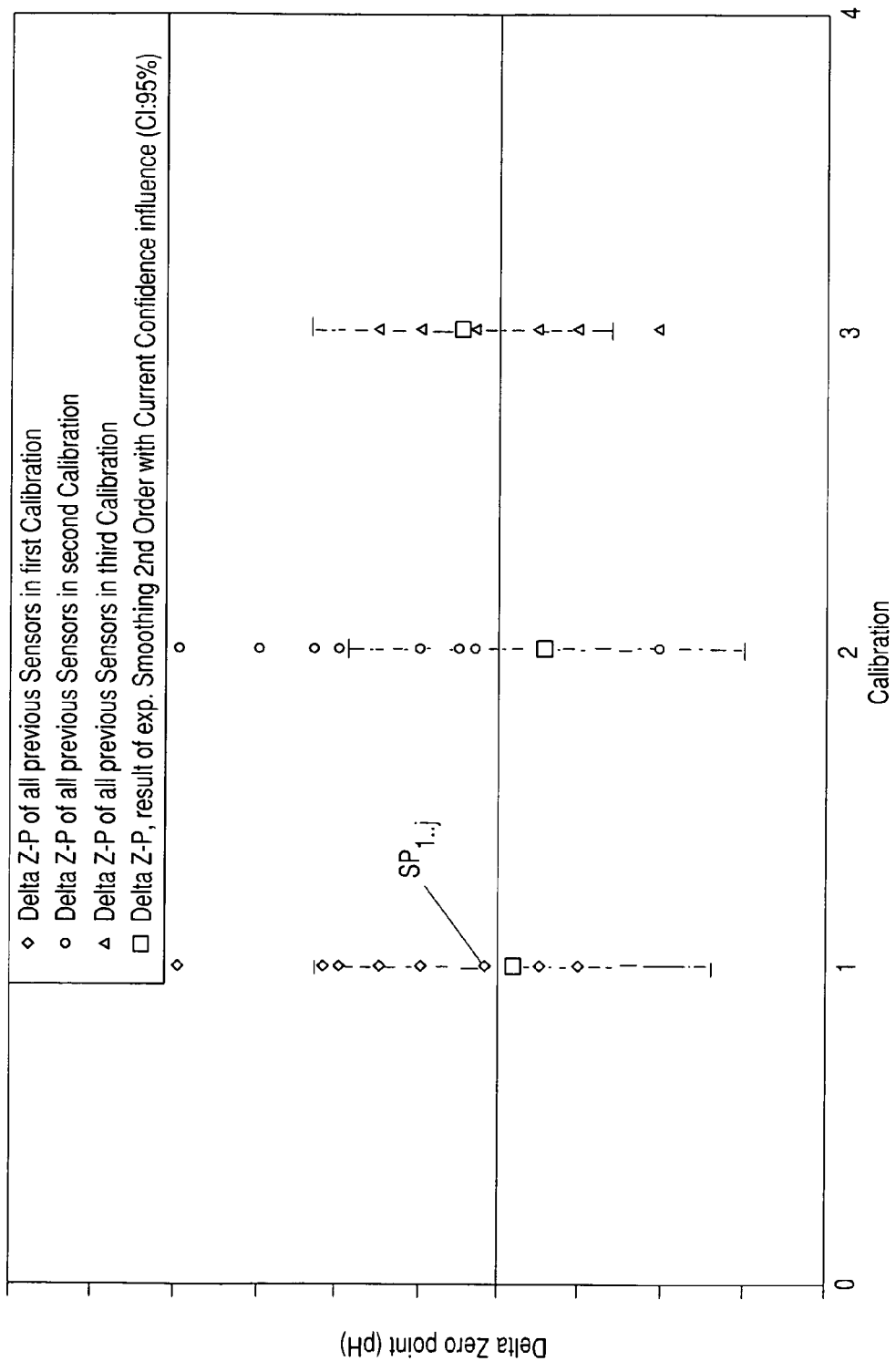
FIG. 4 a drawing of values for shifting of the zero-point for a series of sensor units in the case of three calibration points in time and the current prognosis values ascertained therefrom.

In FIG. 4, values for shifting of the zero-point (delta zero-point) are shown for three different calibration points in time for a number of sensors connected one after the other to the measuring point 201. The values ascertained for the zero point shifting (diamonds) in the case of the first calibrating of the sensors lie in a value range between −0.1 and 0.4. From these values and the newly added value $SP1,j$ of the last connected sensor unit 2.j to the measuring point 201, by means of a sliding, exponential smoothing of 2nd order, a prognosis value is ascertained, which is shown as an open square. Ascertained around this prognosis value is, moreover, a limit value window, which is indicated by dashed line.

In equal manner, presented in FIG. 2 are the shiftings of the zero-point in the case of all sensors used to this point in the case of the second calibrating (circles) and in the case of the third calibrating (triangles) as well as the prognosis values (open squares) and the associated limit value window ascertained from these values.

An option, in the case of determining the prognosis values, is to weight the individual values entering into the calculating. This can happen, for example, by the input of additional information by a service person. The service person can, for example, give when a sensor unit was damaged in a maintenance procedure, or when another disturbance occurred. In this case, one will not, or only with lesser weight, take into consideration the values made available from this sensor unit in the conforming of the prognosis value.

Furthermore, also, in general, i.e. also in the case of the other here described examples of embodiments, a sliding function can be provided in the conforming of the prognosis value. In such case, for example, it can be provided that older sensor data is omitted from the conforming of the prognosis value. For example, the number of sensors, whose values are taken into consideration, can be predetermined. If, for example, a number of five sensors is predetermined, then for conforming the prognosis value only the values of the shifting of the zero-point of the last five sensor units connected to the measuring point 201 are used. Older values can be deleted from the database matrix 5'.

By way of example, here the case was considered, wherein, as diagnostic parameter, the sensor zero point shifting of a pH sensor is used. Equally, alternatively or supplementally, other diagnostic parameters, such as the sensor zero point or the sensor slope, the process parameter of the sensor unit, such as pH value and temperature, or variables derived from these, such as loading equivalents or loading indices, or other sensor-specific parameters, could be considered.

In a third example of an embodiment of the invention, in similar manner, from one or a plurality of diagnostic parameters, a prognosis for the further course, i.e. a trend, of the diagnostic parameter can be ascertained. Through evaluation of a trend of the changing of defined sensor parameters, such as, for example, the changes of zero-point or slope, a remaining service life of a sensor unit can be ascertained. Examples for this are published in DE 10209318 and DE 10239610.

Figure 5:
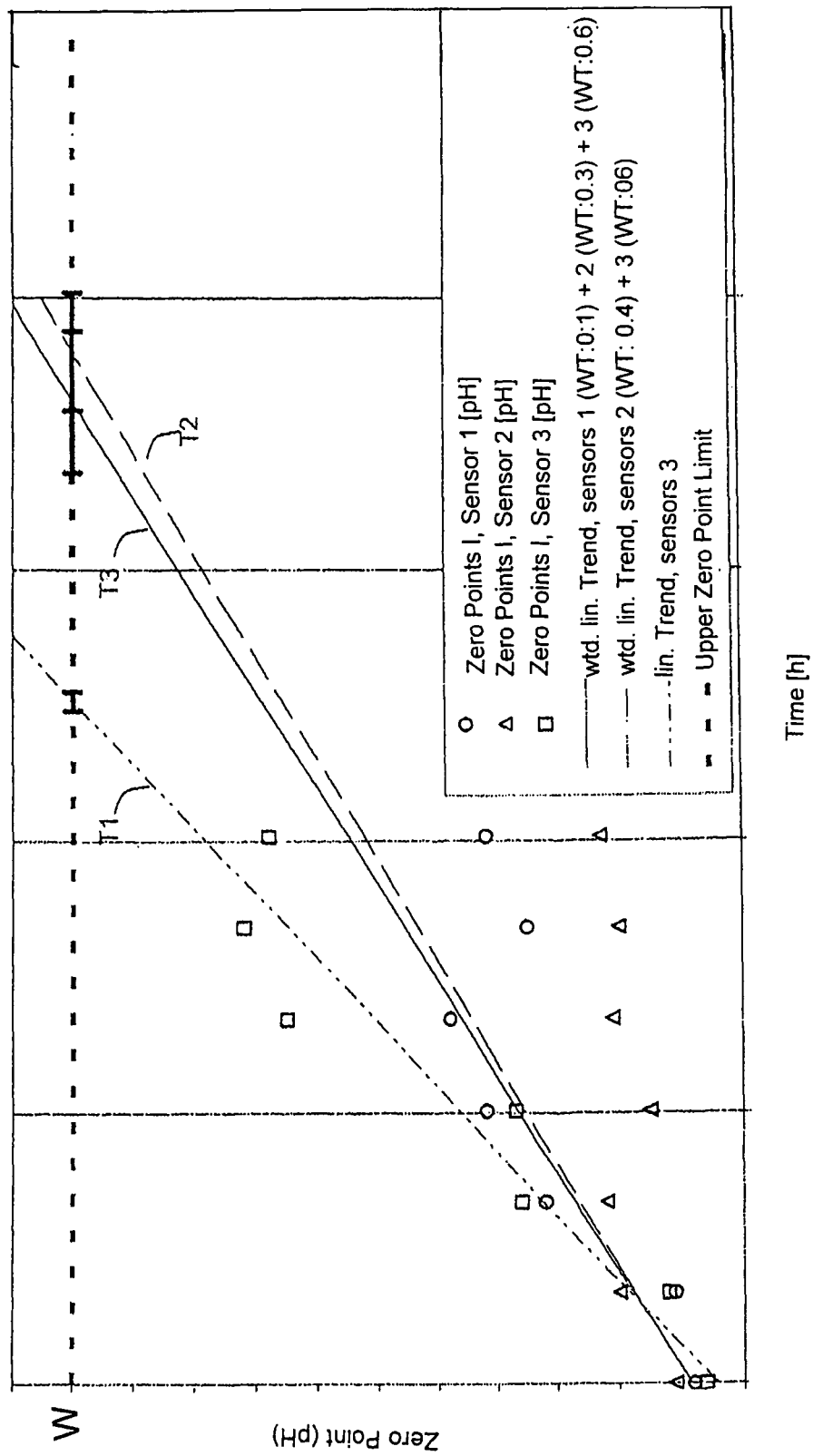
FIG. 5 a drawing of a sequence of zero-point values for three different sensors and the prognosis ascertained therefrom for the zero-point trend for ascertaining a future sensor state.

In the case of operating a measuring point according to the type of measuring point 201 illustrated in FIG. 3, there can be stored in the database matrix 5' values of the sensor zero points of a plurality of sensor units 2.j of the same type at different calibration points in time. In FIG. 5, values for three different sensor units are plotted. In the here illustrated example, all sensor units are calibrated anew in uniform time intervals of 168 hours. It is, however, also possible, that the individual sensor units are calibrated at different points in time. Equally, in the case of a sensor unit, the individual time intervals between the calibrations can be selected differently long.

On the basis of the sensor zero point values, a sensor lifetime, or a remaining service life, can be ascertained as prognosis value. Also, this prognosis value is solid and reliable, the more sensor units are taken into consideration for "learning" the prognosis value.

This is illustrated on the basis of the values of the sensor zero point in FIG. 5 at different calibration points in time for three different sensor units of the same type: First, only the zero point values of a single sensor, the sensor 3 (squares), are taken into consideration for ascertaining a linear trend T1. If one sets a zero point value W as allowable maximum value for the sensor unit, then there results, from the intersection of a line extending parallel to the abscissa through the maximum allowable ordinate value W and the linear trend T1, a prognosis value for the total lifetime, or the remaining service life, of the first sensor unit. This prognosis value is, in turn, surrounded with a confidence interval, or prognosis interval.

The zero point values of a second sensor unit (sensor 2) of the same type as the first sensor unit are shown as triangles. Taking into consideration these zero point values, there results a linear trend T2 having a smaller slope than T1. The learning algorithm used, in this case, a weighted average forming, in the case of which the zero point values of the first sensor unit (sensor 3) are taken into consideration with a weight of only 0.4, while the newer values of the second sensor unit with a weight of 0.6. From the intersection of T2 with the line extending parallel to the abscissa through the predetermined allowable maximum value for the zero-point, there results a conformed prognosis value as well as a conformed confidence interval, or prognosis interval, for the sensor lifetime, which is better suited for further diagnostic purposes, than the interval ascertained on the basis of sensor 3 only.

In analogous manner, the prognosis value for the expected sensor lifetime can be further improved by taking into consideration the zero point values of an additional sensor unit (sensor 1, circles).

Although the invention has been explained essentially on the basis of pH sensors, it is not limited thereto. The method of the invention can be used for any number of measuring points having sensor units of different type, for example, for potentiometric, amperometric, coulometric, colorimetric, photometric, turbidimetric and spectrometric sensor units. Especially, the method of the invention can be used advantageously also at a measuring point having a gas sensor (not illustrated in greater detail), for which as prognosis value, for example, a period of time can be learned, especially, a period of time weighted on the basis of sensor loading, until a membrane must be replaced.

The here described measuring point can be a component of a process monitoring facility, which includes one or a number of similar measuring points. If there are present in the process monitoring facility at least two measuring points, which are exposed to similar or comparable environmental influences, and at which sensor units, which are similar or of the same type are used, it is advantageous, when the respective base units of these measuring points can exchange among one another, for example, via a fieldbus, values stored in their data storage units, especially, values of a diagnostic parameter ascertained by one or a plurality of sensor units, or stored prognosis values, especially prognosis values earlier ascertained by the learning algorithm.

Furthermore, an option is to store, in a central computer of the process monitoring facility, a prognosis value or a prognosis interval in a base unit of a measuring point already solidified and usable through a number of learning cycles, together with information concerning the associated sensor type and concerning specific properties of the measuring point, for which the prognosis value was learned. The specific properties of the measuring point can be stored, for example, in an identification parameter set, which contains information concerning a process class of the process, in which the measuring point is applied, as well as information concerning specific loadings, which act at the measuring point on the sensor, such as e.g. media influences, extreme pH values, extreme temperatures, strong mechanical loading e.g. by a flowing medium, etc.

If, then, a new measuring point is integrated into the process monitoring facility, a new identification parameter set generated for this measuring point is produced. The new identification parameter set can be compared with identification parameter sets stored in the central computer of the process monitoring facility. If the new identification parameter set agrees with a stored identification parameter set essentially completely, the correspondingly stored prognosis value can be used for the new measuring point and stored in the base unit of the new measuring point. This has the advantage, that a first learned prognosis value for one measuring point can be transmitted to similar other measuring points. These measuring points can then either fixedly use the prognosis value or further conform it through other learning steps.

The invention claimed is:

1. A method for operating a measuring point for determining at least one measured variable of a medium, wherein the measuring point comprises a base unit, which is connected releasably with a first sensor unit, and which is provided for communication of a signal representing a value of the measured variable to a process monitoring facility, the method comprises steps of:
   a) at least one-time registering and storing, in the base unit, a value of a diagnostic parameter stored in the first sensor unit or produced by the first sensor unit;
   b) on the basis of said value of the diagnostic parameter stored in the base unit, conforming a prognosis value or prognosis interval stored in the base unit, said prognosis value being a prognosis value of said diagnostic parameter and said prognosis interval is a confidence interval surrounding the prognosis value; and
   c) storing the conformed prognosis value or prognosis interval in the base unit in place of a previously stored prognosis value or prognosis interval, wherein:
   the conforming of the prognosis value or prognosis interval occurring by means of a learning algorithm, which is embodied to learn, over the lifetime of a plurality of sensor units, said prognosis value or prognosis interval:
   said diagnostic parameter is a total loading reserve, a total operating time, operating times under defined conditions or a counter state; and
   said prognosis interval is a confidence interval surrounding the prognosis value;
   wherein a counter state is one of: a counter state for counting cleaning in process (CIP) steps, a counter state for counting sterilization in process (SIP) steps or a counter state for counting autoclaving steps.

2. The method as claimed in claim 1, further comprising a step of:
   d) comparing the value of a diagnostic parameter registered in step a), stored in the base unit, or produced by the first sensor unit, with the prognosis value or prognosis interval stored in the base unit.

3. The method as claimed in claim 2, further comprising:
e) replacing the first sensor unit by a second sensor unit of the same type, and;
f) after replacement of the first sensor unit by the second sensor unit of the same type at least steps a) to (c) are repeated at least once.

4. The method as claimed in claim 3, wherein:
said first and second sensor units are pH-sensor units of the same type.

5. The method as claimed in claim 1, further comprising the step of:
e) replacing the first sensor unit by a second sensor unit of the same type and, after replacement of the first sensor unit by the second sensor unit of the same type, at least steps a) and b) are repeated at least once.

6. The method as claimed in claim 1, wherein:
the learning algorithm comprises a step of average forming, sliding weighted average forming, exponential smoothing of 1st and 2nd type, linear regression, matching of polynomials or matching of non-linear functions.

7. The method as claimed in claim 1, wherein:
at least one additional piece of information is made available to the base unit for ascertaining the prognosis value and;
said additional information comprising a weighting of said diagnostic parameter value.

8. The method as claimed in claim 1, wherein:
said value of said diagnostic parameter is stored in a first data storage unit of the base unit and said prognosis value or prognosis interval and said conformed prognosis value or said conformed prognosis interval are stored in a second data storage unit of the base unit; and
the first data storage unit comprises a memory unit having a plurality of memory locations, and wherein the value of the diagnostic parameter is stored in a memory location together with an identification of the associated sensor unit.

9. The method as claimed in claim 1, further comprising the step of:
d) registering as the diagnostic parameter a parameter related to sensor loading, and, storing as the prognosis value or prognosis interval a parameter, which correlates with a total sensor loading, with which the first sensor unit can be loaded before it must be replaced.

10. The method as claimed in claim 9, wherein:
periodically values of the diagnostic parameter which correlates with the sensor loading are registered one after the other and stored in the base unit.

11. The method as claimed in claim 10, wherein:
in the case of a defective sensor unit, an information, that the first sensor unit is replaced because of a defect, is made available to the base unit.

12. The method as claimed in claim 11, wherein:
after information that the sensor unit is replaced because of a defect has been made available, a last stored value of the parameter which correlates with the sensor loading currently stored in the base unit is used for conforming the stored prognosis value or prognosis interval.

13. The method as claimed in claim 10, further comprising:
e) comparing currently registered values of the diagnostic parameter with the stored prognosis value or prognosis interval.

14. The method as claimed in claim 13, wherein:
a warning message is generated, when one of the periodically registered values of the diagnostic parameter exceeds a lower limit of the prognosis interval stored in the base unit.

15. The method as claimed in claim 1, wherein:
values of a calibration parameter of the first sensor unit are repeatedly registered as values of said diagnostic parameter, and stored in individual locations of a data storage unit of the base unit, together with points in time of registering, or a parameter equivalent thereto, and an identification of the first sensor unit; and
as prognosis values, expected values of the calibration parameter of the first sensor unit at the points in time of registering are stored and conformed on the basis of the registered values of the calibration parameter.

16. The method as claimed in claim 15, wherein:
said first sensor unit is calibrated periodically, and with each new calibration, a value of said calibration parameter is registered and stored.

17. The method as claimed in claim 15, wherein:
the calibration parameter is one of: sensor zero point, sensor slope, sensor zero point shifting or sensor slope shifting.

18. The method as claimed in claim 1, wherein:
said prognosis value or prognosis interval was ascertained from corresponding data of sensor units earlier applied at the measuring point.

19. The method according to claim 1, wherein:
said learning algorithm conforming the prognosis value by ascertaining the conformed prognosis value from said stored value of the diagnostic parameter and from corresponding values of the diagnostic parameter which were ascertained for sensor units earlier applied at the measuring point.

20. The method as claimed in claim 1, further comprising:
d) comparing currently registered values of the diagnostic parameter with the stored prognosis value or prognosis interval; and
e) depending on the position of the value of the diagnostic parameter with reference to the range of the prognosis interval, generating a warning or alarm message on a display of the base unit.

21. The method as claimed in claim 20, wherein:
the warning message is generated, when the value of the diagnostic parameter exceeds a lower limit of the prognosis interval.

22. A method for operating a measuring point for determining at least one measured variable of a medium, wherein the measuring point comprises a base unit, which is connected releasably with a first sensor unit, and which is provided for communication of a signal representing a value of the measured variable to a process monitoring facility, the method comprises steps of:
a) at least one-time registering and storing, in the base unit, a value of a diagnostic parameter stored in the first sensor unit or produced by the first sensor unit;
b) on the basis of said value of the diagnostic parameter stored in the base unit, conforming a prognosis value or prognosis interval stored in the base unit, said prognosis value being a prognosis value of said diagnostic parameter and said prognosis interval is a confidence interval surrounding the prognosis value;
c) storing the conformed prognosis value or prognosis interval in the base unit in place of a previously stored prognosis or prognosis interval;
d) registering as the diagnostic parameter a parameter related to sensor loading, and, storing as the prognosis value or prognosis interval a parameter, which correlates with a total sensor loading, with which the first sensor unit can be loaded before it must be replaced; and e) comparing currently registered values of the diagnostic parameter with the stored prognosis value or prognosis interval, wherein:

the conforming of the prognosis value or the prognosis interval occurring by means of a learning algorithim, which is embodied to learn, over the lifetime of a plurality of sensor units, said prognosis value or prognosis interval;

periodically values of the diagostic parameter which correlates with the sensor loading are registered one after the other and stored in the base unit;

a warning message is generated, when one of the periodically registered values of the diagnostic parameter exceeds a lower limit of the prognosis interval stored in the base unit;

the parameter related to sensor loading is a weighted loading time of the sensor unit;

the parameter correlating with the total sensor loading, with which the sensor unit can be loaded is a total reserve; and the prognosis interval is a confidence interval of the total loading reserve.

23. A method for operating a measuring point for determining at least one measured variable of a medium, wherein the measuring point comprises a base unit, which is connected releasably with a first sensor unit, and which is provided for communication of a signal representing a value of the measured variable to a process monitoring facilty, the method comprises steps of:

a) at least one-time registering and storing, in the base unit, a value of a diagnostic parameter stored in the first sensor unit or produced by the first sensor unit;

b) on the basis of said value of the diagnostic parameter stored in the base unit, conforming a prognosis value or prognosis interval stored in the base unit, said prognosis balue being a prognosis value of said diagnostic parameter and said prognosis interval is a confidence interval surrounding the prognosis value; and c) storing the conformed prognosis value or prognosis interval in the base unit in place of a previously stored prognosis value or prognosis interval, wherein:

the conforming of the prognosis value or prognosis interval occurring by means of a learning algorithim, which is embodied to learn, over the lifetime of a plurality of sensor units, said prognosis value or prognosis interval;

values of a calibration parameter of the first sensor unit are repeatedly registered as values of said diagnostice parameter, and stored in individual location of a data storage unit of the base unit, together with points in time of registering, or a parameter equivalent thereto, and an identification of the first sensor unit;

as prognosis values, expected values of the calibration parameter of the first sensor unit at the pints in time of registering are stored and conformed on the basis of the registered values of the calibration parameter; and as prognosis intervals a limit value window around the expected values of the calibration parameter are stored and conformed on the basis of the registered values of the calibration parameter.

24. The method as claimed in claim 23, further comprising:

d) comparing currently registered values of the calibration parameter with the stored prognosis values or prognosis intervals.

25. The method as claimed in claim 24, wherein:

a warning message is generated, when one of the periodically registered values of the diagnostic parameter exceeds a lower limit of the prognosis interval.

* * * * *